United States Patent
Machavariani et al.

(10) Patent No.: US 6,885,446 B2
(45) Date of Patent: Apr. 26, 2005

(54) METHOD AND SYSTEM FOR MONITORING A PROCESS OF MATERIAL REMOVAL FROM THE SURFACE OF A PATTERNED STRUCTURE

(75) Inventors: Vladimir Machavariani, Rishon Lezion (IL); David Scheiner, Ganei Yehuda (IL); Amit Weingarten, Ramat Gan (IL); Avi Ravid, Cupertino, CA (US)

(73) Assignee: Nova Measuring Instruments Ltd., Rehovot (IL)

( * ) Notice: Subject to any disclaimer, the term of this patent is extended or adjusted under 35 U.S.C. 154(b) by 328 days.

(21) Appl. No.: 10/309,348

(22) Filed: Dec. 4, 2002

(65) Prior Publication Data

US 2003/0155537 A1 Aug. 21, 2003

(30) Foreign Application Priority Data

Dec. 4, 2001 (IL) .................................................. 146924

(51) Int. Cl.$^7$ ................................................ G01J 3/42
(52) U.S. Cl. ...................................... 356/319; 356/504
(58) Field of Search ................................ 356/319, 504, 356/630; 250/559.27; 451/6

(56) References Cited

U.S. PATENT DOCUMENTS

| | | | |
|---|---|---|---|
| 4,741,620 A | 5/1988 | Wickramasinghe | |
| 5,471,305 A | 11/1995 | Yoneda et al. | |
| 5,517,312 A | 5/1996 | Finarov | |
| 5,563,706 A | 10/1996 | Shibuya et al. | |
| 5,905,572 A | * 5/1999 | Li | 356/450 |
| 6,100,985 A | 8/2000 | Scheiner et al. | |
| 6,184,994 B1 | 2/2001 | Freischlad | |
| 6,281,974 B1 | 8/2001 | Scheiner et al. | |
| 6,292,265 B1 | * 9/2001 | Finarov et al. | 356/630 |
| 6,306,669 B1 | 10/2001 | Yano et al. | |
| 6,369,375 B1 | * 4/2002 | Ishiwata | 250/225 |
| 6,727,501 B1 | * 4/2004 | Fan et al. | 250/307 |
| 6,744,517 B1 | * 6/2004 | Forno et al. | 356/450 |
| 6,753,972 B1 | * 6/2004 | Hirose et al. | 356/630 |
| 2002/0057437 A1 | * 5/2002 | McMillen et al. | 356/504 |

FOREIGN PATENT DOCUMENTS

WO      WO 01/77629 A2      10/2001

OTHER PUBLICATIONS

Ravid et al., "Copper CMP Planarity Control Using ITM", Sep. 12–14, 2000, 2000 IEEE/SEMI Advanced Semiconductor Manufacturing Conference and Workshop, pp. 437–443.*

* cited by examiner

Primary Examiner—Zandra Smith
Assistant Examiner—Kara Geisel
(74) Attorney, Agent, or Firm—Browdy and Neimark, P.L.L.C.

(57) ABSTRACT

A method and system are presented for use in controlling a process of material removal from the surface of a patterned structure, by measuring at least one of residue, erosion, dishing and corrosion effects in the structure induced by this process. The structure is imaged utilizing phase modulation of light reflected from the structure, and a phase map of the structure is thereby obtained. This phase map is analyzed and data indicative of light reflective properties of layer stacks of the structure is utilized to determine a phase difference between light reflected from a selected measured site and at least one reference site spaced-apart from the selected site. The phase difference is thus indicative of the measured effect.

43 Claims, 8 Drawing Sheets

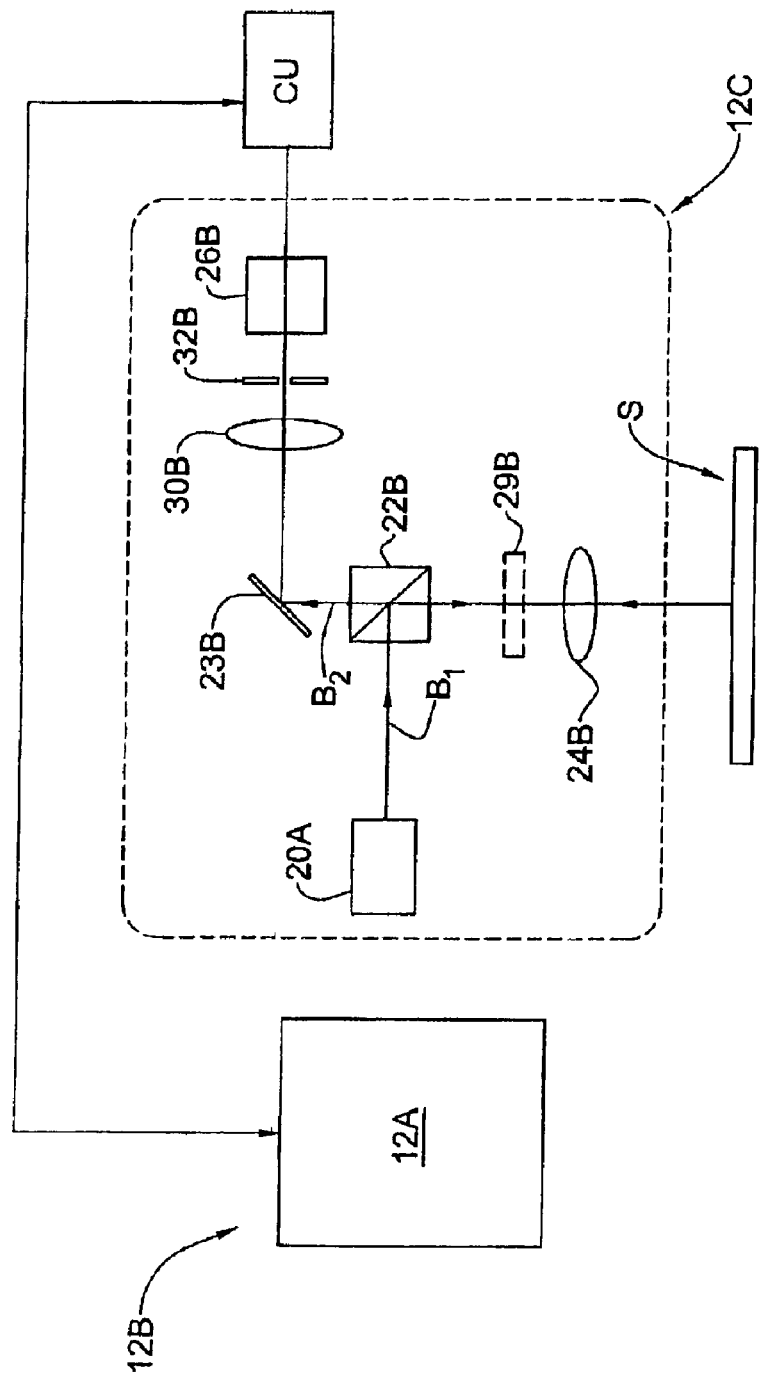

METHOD AND SYSTEM FOR MONITORING A PROCESS OF MATERIAL REMOVAL FROM THE SURFACE OF A PATTERNED STRUCTURE

FIELD OF THE INVENTION

This invention is in the field of optical monitoring techniques, and relates to a method and system for monitoring a process of material removal from the surface of a patterned structure, such as a process of chemical mechanical planarization (CMP). The invention is particularly useful in the manufacture of semiconductor devices.

BACKGROUND OF THE INVENTION

The process of material removal from the surface of a pattern structure (such as a semiconductor wafer) might lead to such undesirable effects as residue, dishing, erosion and corrosion. Timely detection of these effects can be used for controlling the material removal process.

In the manufacture of semiconductor devices, aluminum has been used almost exclusively as the main material for interconnects. However, recent developments in this field of the art have shown that copper is posed to take over as the main on-chip conductor for all types of integrated circuits. Compared to aluminum, copper has a lower resistance, namely less than 2 $\mu\Omega$-cm even when deposited in narrow trenches, versus more than 3 $\mu\Omega$-cm for aluminum alloys. This lower resistance is critically important in high-performance microprocessors and fast static RAMs, since it enables signals to move faster by reducing the so-called "Resistance-Capacitance" (RC) time delay. Additionally, copper has a superior resistance to electromigration, which leads to lower manufacturing costs as compared to aluminum-based structures.

During the manufacture of semiconductor devices, a wafer undergoes a sequence of photolithography-etching steps to produce a plurality of patterned layers (stacks). Then, depending on the specific layers or production process, the uppermost layer of the wafer may or may not undergo a CMP process to provide a smooth surface of this layer. This is true for the copper-based or tungsten-based structures, and also for the aluminum-based semiconductor structures in which aluminum has been deposited by the dual Damascene process.

Copper has properties that add to the polishing difficulties. Unlike tungsten, copper is a soft metal and subject to scratching and embedding particles during polishing. Additionally, owing to the fact that copper is highly electrochemically active and does not form a natural protective oxide, it corrodes easily. With conventional technology of planarization, ILD polishing occurs after every metal deposition and etch step. The same is not true for damascene processing, wherein the post-polish surface is, expected to be free of topography. However, topography is induced because of erosion of densely packed small feature arrays and dishing of the metal surface in large features.

Copper CMP is more complex because of the need to completely remove the tantalum or tantalum nitride barrier layers and copper uniformity without the overpolishing of any feature. This is difficult because current copper deposition processes are not as uniform as the oxide deposition process. Additionally, tolerances for erosion and dishing are much narrower for copper CMP.

The effects of residues, dishing and erosion present defects on the wafer induced by the CMP process applied thereto. Dishing and erosion may deteriorate the interconnections' quality, especially when the copper thickness is reduced. Indeed, the reduction of the copper thickness results in the increase of RC constants, resulting in the slower functioning of the integrated circuit. As indicated above, the lower resistance is critically important in high-performance microprocessors and fast static RAMs. The ability to monitor the level of residues, dishing and erosion can enable tighter control of the CMP process.

CMP of dielectric layers can also lead to the pattern dependent non-planarity effects, such as erosion and dishing. An example of the dielectric CMP is the shallow trench isolation (STI) process, which forms silicon dioxide isolation channels surrounding the silicon nitride covered active transistor areas. Here, the surface non-planarity is caused owing to the fact that different dielectric materials of the structure exposed to the polish process are removed with different rates. Silicon dioxide areas typically undergo enhanced removal relative to the adjacent silicon nitride areas. In large silicon dioxide features, this results in dishing; in densely patterned areas, the CMP process can erode both the silicon nitride and silicon dioxide features. Overpolishing usually results in an increased dishing, while under-polishing results in residues over the silicon nitride areas.

SUMMARY OF THE INVENTION

There is a need in the art to facilitate controlling a CMP process applied to patterned structures, such as semiconductor wafers, by providing a novel method and system for non-contact, optical measurements of at least one of dishing, erosion, and residue effects on the patterned structure induced by the CMP process applied thereto.

The term "patterned structure" used herein signifies a multi-layer structure having spaced-apart regions of different optical properties defined by different layer stacks. Different layer stacks are stacks formed by different materials and/or defining surface regions of different dimensions.

The main idea of the present invention consists of using an optical system capable of phase mapping of the structure's surface applied to selected areas of the structure. The phase mapping may utilize interferometric measurements. The latter may be based on using a first static reference beam that impinges on a reference site, and a second beam that scans the area of interest, or may be based on the use of a static reference beam that impinges on a large flat reference surface and a second beam that, while mapping (imaging) the area of interest, interferes with the beam from the reference surface. Other phase mapping techniques are also available.

Some particulars and examples of the phase mapping (imaging) technique that are suitable to be used in the present invention are disclosed in WO0177629. Another example of the suitable apparatus for phase mapping (imaging) is Wyko Optical Metrology Module (OMM), commercially available from Digital Instruments/Veeco Metrology, USA.

The optical system of the invention may utilize a combination of the phase map (imaging) technique and spectrophotometric measurements. Both, the polarized and un-polarized phase mapping can be used. The spectrophotometric measurements may be performed by any known systems, for example NovaScan 2020/3030 commercially available from Nova Measuring Instruments Ltd., Israel. The particulars of the measuring technique that may be utilized in the present invention for measurements on patterned structures (sites) are disclosed in U.S. Pat. Nos. 6,100,985 and 6,281,974, both assigned to the assignee of the present application.

For metal CMP the present invention takes an advantage of the fact that while illuminating a site in a patterned structure having metal-containing regions (substantially reflective regions) on its surface, light reflected from this site is substantially not affected by, the parameters of underneath layers in the structure. Consequently, by introducing phase modulation to light reflected from at least two spaced-apart sites, relative dishing erosion or residue effects between these sites can be detected. It should be understood that "dishing" and "erosion" effect exemplify the so-called "over-removal" (e.g., over-polishing) of the upper layer material, in, respectively, differently patterned sites, while "residue" exemplifies the insufficient removal (e.g., under-polishing) of the upper layer material. When one of the measured sites has a very small dishing or erosion effect, as compared to the other site, this measurement is an almost absolute measurement of the respected effect.

For dielectric CMP, especially at the lower process steps such as STI, the present invention takes an advantage of the fact that while illuminating a site in a patterned structure, relatively simple optical models can be utilized to extract the relevant parameters of the light reflection properties. Consequently, by introducing phase modulation to the light reflected from at least two spaced-apart sites, relative dishing, erosion or residue effects between these sites can be detected. It should be understood that "dishing" and "erosion" effect exemplify the so-called "over-removal"(e.g., over-polishing) of the upper layer material, in, respectively, differently patterned sites, while "residue" exemplifies the insufficient removal (e.g., under-polishing) of the upper layer material.

Thus, according to one broad aspect of the present invention, there is provided a method for use in controlling a process of material removal from the surface of a patterned structure, by measuring at least one of residue, erosion, dishing and corrosion effects in the structure, the method comprising:

imaging, the structure utilizing phase modulation of light reflected from the structure, thereby obtaining a phase map of the structure;

analyzing said, phase map while utilizing data indicative of light reflective properties of layer stacks of the structure to determine a phase difference between light reflected from a selected site in the structure and at least one reference site in the structure spaced-apart from said selected site, said phase difference being indicative of the measured effect in at leas the selected site.

The measured phase difference may be informative of a relative value of the measured effect in the selected site as compared to the at least one reference site. When the at least one reference site has a relatively small value of the measured effect, the measure d phase difference is informative of an absolute value of the, measured effect in the selected site.

The invented method may also comprise spectrophotometric measurements applied to the at least one reference site and possibly also to the selected site. Data indicative of the light reflective properties of layer stacks of the structure is extracted for a selected wavelength, which is the same as that used for the phase mapping. The selected wavelength of the phase mapping can be within or outside the wavelength range of the spectrophotometric measurement. Imaging the structure utilizing the phase modulation can be performed using non-polarized or polarized light. Independently, the spectrophotometric measurement can be performed using non-polarized or polarized light. By this, influence of the parameter of layer stacks of the structure (i.e., of the reflectivity properties) onto said phase difference can be determined, thereby enabling determination of the absolute value of the measured effect at least in the selected site.

The method of the present invention provides for detecting the presence of residue effects, and/or corrosion in the case of metal-containing structures, by using the phase mapping of a golden structure, which is a structure constructed similarly to the measured structure, but having no such effects.

According to another broad aspect of the present invention, there is provided a method for use in controlling a process of material removal from the surface of a patterned structure, by measuring at least one of residue, erosion, dishing and corrosion effects in the structure, the method comprising:

imaging the structure utilizing phase modulation of light reflected from the structure, thereby obtaining a phase map of the structure;

applying spectrophotometric measurements to at least one reference site of the structure spaced-apart from a selected site of the structure, thereby obtaining measured data indicative of the intensities of light reflected from the at least one reference site of the structure as a function of wavelength of incident light properties of a layer stack of the structure in said at least one reference site;

analyzing said phase map to determine a phase difference between light reflected from different sites of the structure, and analyzing said measured data to determine an effect of the reflective properties of a layer stack in said at least one reference site onto said phase difference at the wavelength used for the phase mapping, and thereby determine an absolute value of the measured effect in at least the selected site of the structure.

According to yet another broad aspect of the present invention, there is provided an optical system for use in controlling a process of material removal from the surface of a patterned structure, to determine at least one of residue, erosion, dishing and corrosion effects in the structure, the system comprising:

an imaging system having an illuminator unit, a detector unit, and a light directing arrangement for directing incident light to the structure and directing light reflected from the structure to the detector unit, the light directing arrangement comprising a phase modulator accommodated in optical path of the reflected light propagating to the detector, an output of the detector being in the form of at least one intensity map; and a control unit connectable to the imaging system and operable to receive the output of the detector and process it to obtain data indicative of a phase map of the structure, the control unit having a data processing and analyzing utility operating to analyze the phase map to determine at least one of the following:

the value of at least one of the erosion and dishing effects in a selected site of the structure, determined by a phase difference between the selected site and a reference site of the structure spaced-apart from said selected site, wherein said reference site has a relatively small value of the measured effect as compared to that of the selected site;

a difference $\Delta DD$ of the dishing effects between a selected site of the structure and a relatively small reference site of the structure spaced-apart from the selected site;

an absolute value of the dishing effect in the selected site which is relatively large as compared to, a reference site of the structure spaced-apart from the selected site, by utilizing correlation between the difference ΔDD and an absolute value of the dishing effect, a difference ΔED between the dishing and erosion effects in a selected site of the structure and a reference site of the structure spaced-apart from the selected site;

absolute values of the dishing and erosion effects in the selected and reference sites, by utilizing correlation between the difference ΔED and absolute value of the dishing and erosion effects;

a difference of the erosion effects between a selected patterned site of the structure and a relatively small, reference patterned site of the structure;

a difference ΔEE between the erosion effects in a selected site of the structure and a reference site spaced-apart from the selected site;

an absolute, value of the erosion effect in said selected site utilizing correlation between the difference ΔEE and an absolute value, of the erosion effect;

presence of defects or corrosion effect in the structure;

presence of residue effect in the structure.

According to yet another aspect of the present invention, there is provided an optical system for use in controlling a process of material removal from the surface of a patterned structure, to determine, at least one of residue, erosion, dishing and corrosion effects in the structure, the system comprising:

an imaging system having an illuminator unit, a detector unit, and a light directing arrangement for directing incident light to the structure and directing light reflected from, the structure to the detector unit, the light directing arrangement comprising a phase modulator accommodated in optical path of the elected light propagating to the detector, an output of the detector being in the form of at least one intensity map;

a spectrophotometer, system operable for applying spectrophotometric measurements to at least one reference site of the structure spaced-apart from a selected site of the structure and thereby obtaining output in the form of intensities of light reflected from the at least one reference site of the structure as a function of wavelength of incident light; and a control unit connectable to the imaging system and to the spectrophotometer system, and operable to receive the output of these systems and process them to obtain data indicative of a phase map of the structure and data indicative of the reflective properties of a layer stack of the structure in the at least one reference site, the control unit having a data processing and analyzing utility operating to determine at least one of the following:

an absolute value of the dishing effect in the selected site;

an absolute value of the erosion effect in the selected site having the pattern characterized by at least one of a small pitch and a large metal duty cycle (DC) value;

a difference ΔDD of the dishing effects between the selected site and the relatively small reference site;

an absolute value of the dishing effect in the selected site, by utilizing correlation between the difference ΔDD and an absolute value of the dishing effect;

a difference ΔED between the dishing and erosion effects in the selected and reference sites;

an absolute value of one of the dishing and erosion effects utilizing correlation between the difference ΔED and an absolute value of one of the dishing and erosion effects;

a difference ΔEE between the erosion effects in the selected and reference sites of the structure;

absolute values of the erosion effect in the selected site utilizing correlation between the difference ΔEE and an absolute value of the erosion effect;

presence of defects or corrosion effect in the structure;

presence of residue effect in the structure.

More specifically the present invention is used for controlling a material removal process (such as CMP) applied to a semiconductor wafer structure and is therefore described below with reference to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A and 3B schematically illustrate two examples, respectively, of the optical system according to the invention;

DETAILED DESCRIPTION OF THE INVENTION

Figure 1:
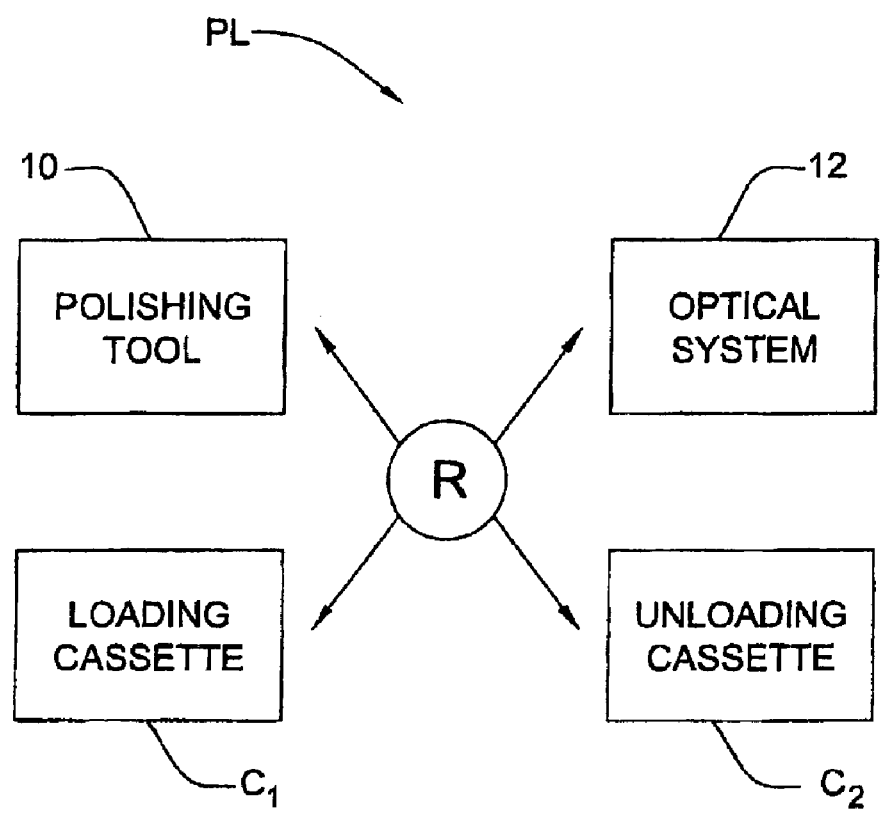
FIG. 1 is a schematic illustration of a part of a production line utilizing an optical measurement system according to the invention.

Referring to FIG. 1, there is illustrated a part of a production line PL for the manufacture of copper-based patterned structures (wafers) utilizing the measurement technique according to the invention. The wafer structure is a stack-layer structure, for example resulting from typical Cu dual damascene process, as will be described more specifically further below with reference to FIGS. 2A and 2B. The production line part PL includes a CMP, polishing pad 10, loading and unloading cassettes $C_1$ and $C_2$, a robot R, and an optical measurement system 12. The robot R conveys wafers between the polishing assembly 10 and the measurement system 12. The construction and operation of the CMP polishing assembly 10 are known per se and therefore need not be specifically described. As for the measurement system 12, its construction and operation will be described below with reference to FIGS. 3A and 3B.

Figure 2A:
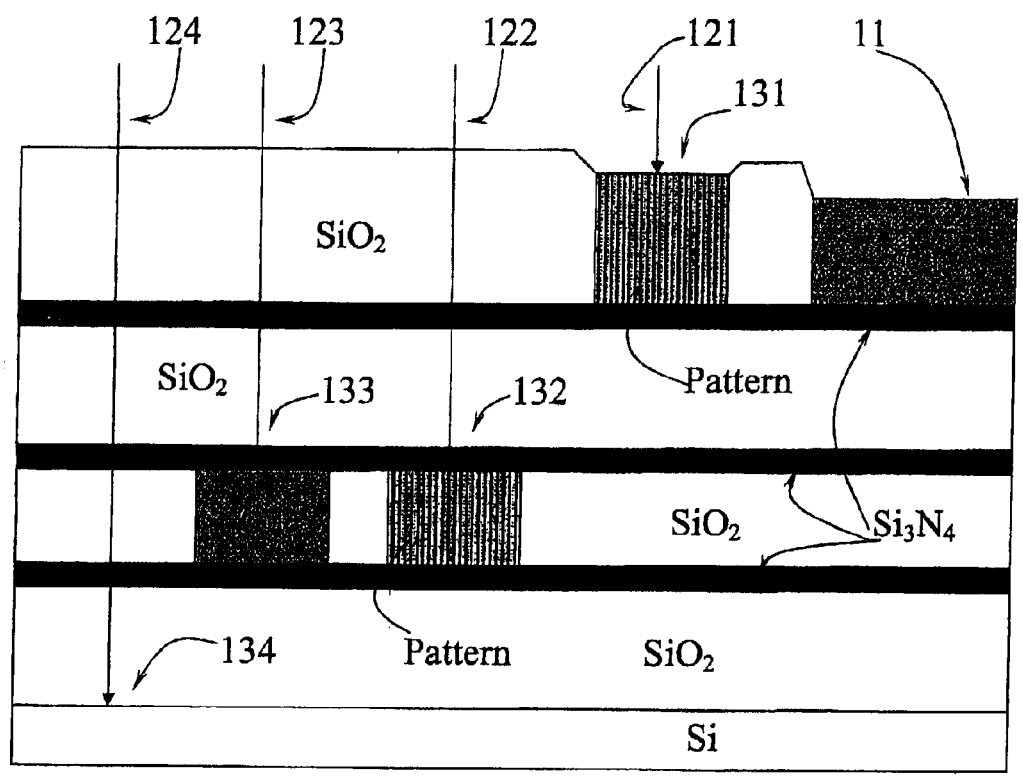
FIGS. 2A and 2B schematically illustrate two examples, respectively, of the cross-section of a typical Cu dual damascene process.
Figure 2B:
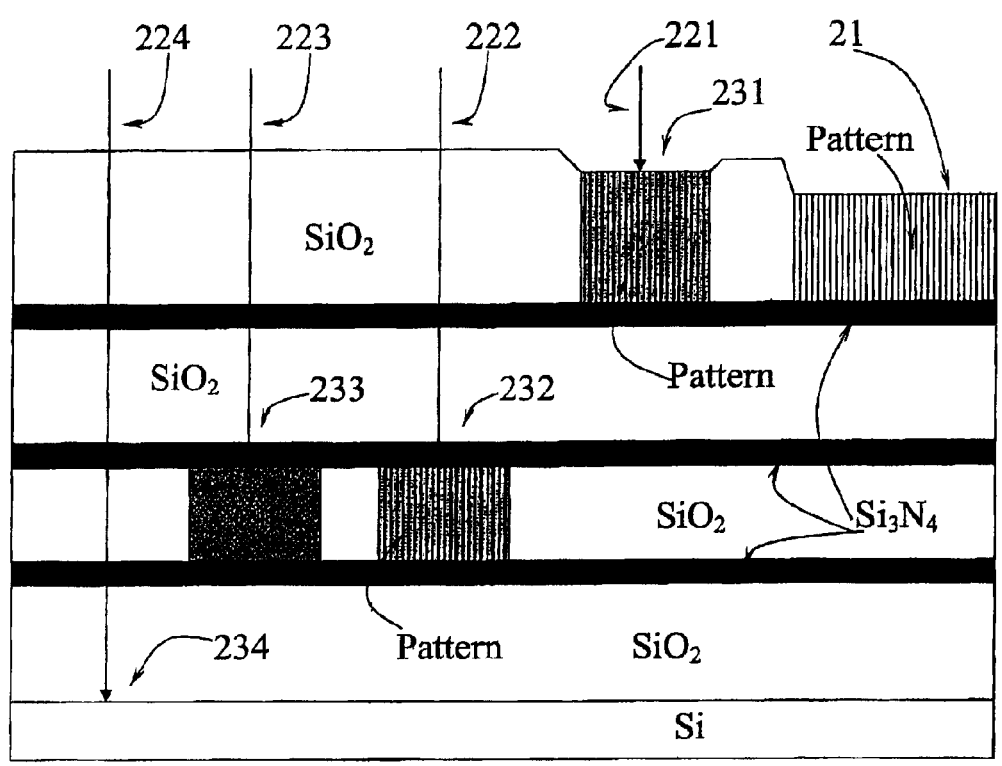

FIGS. 2A and 2B illustrate schematically two examples of the cross-section of a structure S in the typical Cu dual damascene process. In the, example of FIG. 2A, the structure S has several reference stacks 131, 132, 133, and 134, and a metal pad 11 (copper in the present example) that is a pad (site) of interest (constituting a selected site). Reference stack 131 has a patterned area in the upper layer, reference stack 132 has a patterned area in the lover layers, reference stack 133 has a Cu pad in the lower layers and reference stack 134 is transparent down to a Si substrate.

In the example of FIG. 2B, the, structure S has several reference stacks 231, 232, 233, and 234 and a patterned pad 21 (copper lines in the oxide or low-k matrix in the present example) that is a pad of interest Reference stack 231 has a patterned area in the upper layer, reference stack 232 has a patterned area in the lower layers, reference stack 233 has a Cu pad in the lower layers, and reference stack 234 is transparent down to a Si substrate.

Figure 2C:
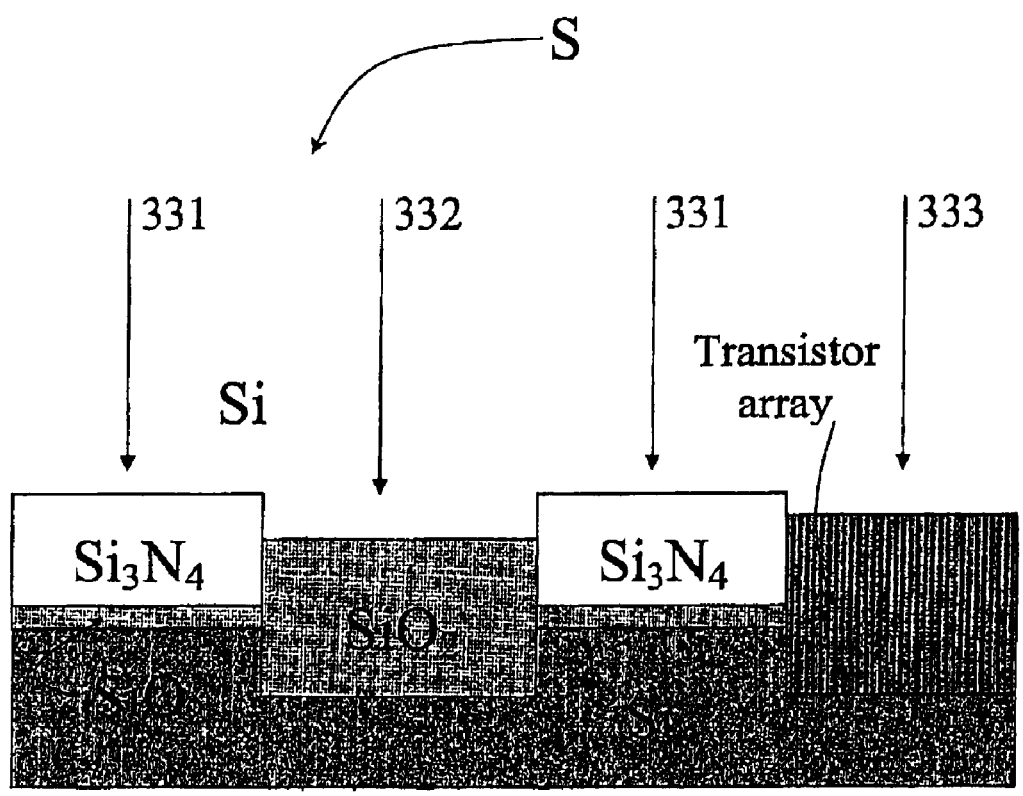
FIG. 2C schematically illustrate an example of the cross-section of a typical shallow trench isolation (STI) process.

FIG. 2C illustrates schematically an example of the cross-section of a structure S in the typical STI process. In this example, the structure S has several stacks 331, 332, and 333, wherein stack 331 is the reference stack and stacks 332 and 333 are stacks (sites) of interest, i.e., to be measured. Reference stack 331 has a silicon nitride, stack 332 has a silicon dioxide area above a trench in silicon, and stack 333 has a patterned area consisting of silicon nitride and silicon dioxide regions.

Figure 3A:
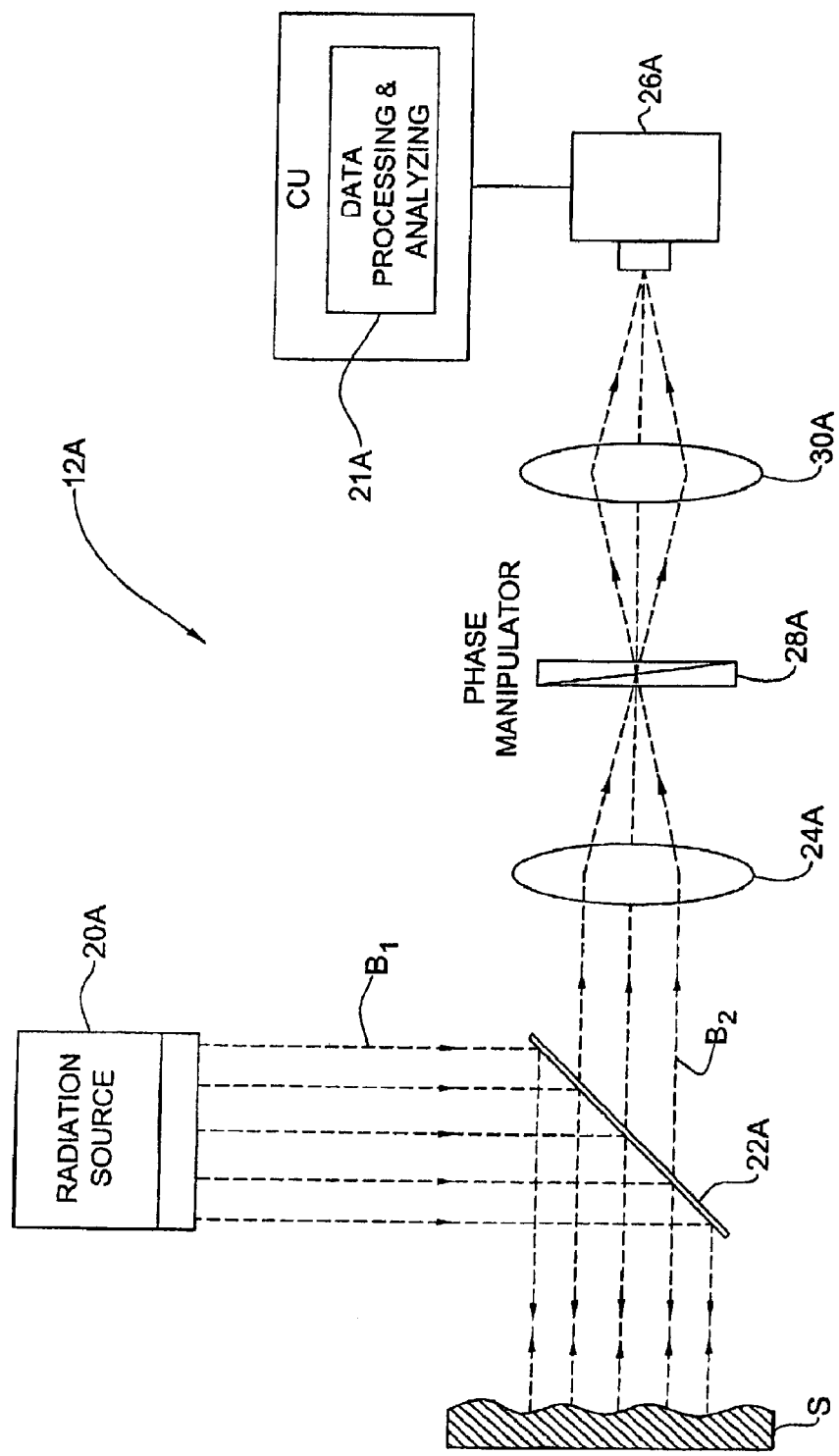

FIGS. 3A and 3B schematically illustrate two examples of the optical monitoring system according to the, invention designed to carry our, respectively, the phase mapping (three-dimensional imaging) of the surface of the structure S within selected areas (sites) of the structure, and a combination of the phase mapping and spectrophotometric measurement.

The system 12A of FIG. 3A comprises an illuminator unit 20A; a light directing arrangement, detector 26A (e.g., CCD); and a control unit CU that includes inter alia a data processing and analyzing utility 21A. The illuminator 20A (optionally including a beam expander) produces an illuminating beam $B_1$ to impinge onto the structure and thereby produce light $B_2$ reflected from the structure. The light directing arrangement includes a beam splitter 22A, which reflects the illuminating light onto the patterned surface S to be imaged and transmits the returned light towards the detector 26A; lenses 24A and 30A; and a phase manipulator 28A between the lenses. Illuminating light $B_1$ may be either randomly polarized or of specific polarization. The reflected light $B_2$ is a three-dimensional imaging wavefront, which has amplitude and phase, and which contains information about the surface relief of the patterned surface S. At least a part of the reflected light is transmitted from the beam splitter 22A and focused by the lens 24A onto the phase manipulator 28A, which is preferably located at the image plane of the radiation source 20A. The phase manipulator 28A may for example be a spatial light modulator or a series of different transparent spatially non-uniform objects. The phase manipulator 28A can be configured such that a substantial part of the radiation focused onto the manipulator 28A is either reflected therefrom or transmitted therethrough. The second lens 30A is arranged so as to image the structure's surface onto the detector 26A. Preferably, the second lens 30A is arranged such that the detector 26A is located in its focal plane. The output of the detector 26A, for example in the form of a set of intensity maps, is supplied to the control unit CU. There, the output of the detector is processed to obtain information indicative of the phase map of light returned from the structure.

The illuminating beam $B_1$ may have a narrow wavelength band about a given central wavelength, causing the phase of the radiation reflected from structure to be proportional to geometrical variations in the structure's surface, the proportion being an inverse linear function of the central wavelength of the radiation. The beam $B_1$ may have at least two narrow wavelength bands, each centered about a different wavelength, in which case the reflected light $B_2$ has at least two wavelength components, each centered around the respective wavelength and at least two indications of the phase of the three-dimensional imaging wavefront are obtained, each indication corresponding to a different wavelength component of the reflected light. These at least two indications may be subsequently combined to enable enhanced imaging of the structure's surface, by avoiding two ambiguity in the three-dimensional imaging.

The phase manipulator 28A may apply a plurality of different spatial phase changes to the radiation wavefront reflected from structure's surface and Fourier transformed by the lens 24A. Application of the plurality of different spatial phase changes provides a plurality of differently phase changed transformed wavefronts, which may be subsequently detected by the detector 26A. Different spatial phase changes can be applied by the phase manipulator 28A, resulting in a corresponding number of different intensity maps, which are processed at the control unit to obtain an output indicating at least the phase of the three-dimensional imaging wavefront. Additionally, the illuminating light beam $B_1$ may comprise a plurality of different wavelength components, thereby providing a plurality of wavelength components in the three-dimensional imaging wavefront and subsequently in the transformed wavefront impinging on the phase manipulator 28A. In this case, the phase manipulator 28A may be an object with spatially varying thickness and/or refractive index and/or surface geometry. This spatial variance of the phase manipulator generates a different spatial phase change for each of the wavelength components, thereby providing a plurality of differently phase changed transformed wavefronts to be subsequently detected by detector 26A. The system 12A is generally similar to that disclosed in the above-indicated publication WO 01/77629, which is therefore incorporated herein by reference with respect to this specific example.

The system 12B of FIG. 3B comprises the optical system 12A (or any other suitable imaging system of the kind capable of obtaining a phase map of the structure) and a spectrophotometer arrangement 12C, both connectable to a control unit CU. It should be, understood that the processing and analyzing utilities associated with the systems 12A and 12C may be parts of different control units. The spectrophotometer includes a light source 20B for generating a beam of light $B_1$ of a predetermined wavelength range; light directing optics; and a detector 26B. The light directing optics comprises an objective lens 24B, a beam splitter 22B, a mirror 23B, and an imaging lens 30B. Optionally provided is a variable aperture stop 32B. Also optionally provided in the spectrophotometer 12C is a polarizer 29B (shown in dashed lines) accommodated in the optical path of illuminating light, for example between the beam splitter 22B and the objective lens 24B. It should be understood that of illumination of a structure with polarized light is needed the same can alternatively be achieved by using a light emitting device of the kind generating polarized light.

The construction and operation of the spectrophotometer arrangement may be of anger known kind, for example such as disclosed in U.S. Pat. No. 5,517,312 assigned to the assignee of the present application. The light beam $B_1$ passes through the light directing optics and impinges onto the structure S at a certain location (site) defining a measurement area $S_1$ (e.g., of about 20 μm in size). Light $B_2$ specularly reflected from the reflective regions within the area $S_1$ is directed onto the detector 26B. It should be noted that, generally the illuminated location of the structure may be larger than the measurement area $S_1$, in which case suitable optics are provided for capturing, in a conventional manner, light reflected solely from the part (area $S_1$) within the illuminated location. The spectrophotometer system measures the photometric intensities of different wavelengths contained in the detected light component of the reflected beam $B_2$. The control unit CU comprises suitable pattern recognition software and translation means so as to be responsive to the spectrophotometric measured data and locate measurements.

Generally, the technique of the present invention is based on determining the phase difference in the light signals returned (reflected) from two different sites on the structure, at least one of the sites being the site of interest, i.e., where a dishing/erosion/residue effect is more likely to occur. When it can be predicted that the phase difference is not affected by lower layers in the stacks at both sites or the stack affect at one site is very similar to that at the other site, then applying the phase mapping is practically sufficient of measuring the dishing/erosion/residue effect. When the underlying layers structure can affect the phase difference, data indicative of the layers' effect is to be determined, namely, the phase of the detected reflected signal is to be determined (reference stack parameters), which can be implemented by spectrophotometric measurements. For sites that are larger than the field of view of the phase imaging device, the nearest fields can be measured with some overlap and glued together. As a result, the "mosaic" phase image can be constructed, which is larger than the field of view of the phase-map-measuring device. The following are some examples of the monitoring technique of the present invention.

EXAMPLE 1

Absolute Dishing Measurement as a Combination of Phase Mapping (Imaging) and Spectrophotometric Measurement To implement this measurement the optical system of FIG. 3B is applied to the structure of FIG. 2A or FIG. 2C.

Step 1: Spectrophotometric measurement allows extraction of data about the reference stack parameters (i.e., reflective properties of the layer stacks in the measured sites). Using these stack parameters, the phase $\phi_{UP}$ of the reflected wave at the upper interface of the reference stack can be calculated. Reference pad can be either in the upper layer (pad 131 in FIG. 2A or pad 331 in FIG. 2C), or in the underneath layers of the structure (pads 132 and 133 in FIG. 2A). Spectrophotometric measurement is applied to the selected site (site of interest), which is a pad in the dishing measurement application, i.e., the pad 11 in FIG. 2A or pad 332 in FIG. 2C in the present examples, and applied to at least one of the following points (reference sites): point 331 and 332 in the example of FIG. 2C; point 121 (for stack 131), point 122 (for stack 132), 123 (for stack 133), and point 124 (for stack 134) in the example of FIG. 2A. Measured spectrum is analyzed and the parameters of the respective stack are determined. Using calculated parameters, the phase shift of the reflected wave $\phi_{UP}$ at the upper interface is calculated for a selected wavelength λ. More specifically, in the case of stack of non-patterned layers, the phase is determined as follows (modulus 2π):

$$\phi_{UP} = \text{Phase}(R(0)) \quad (1)$$

wherein R is the total reflection from the structure determined using the following recurrent equation:

$$R(j) = \frac{r(j) + R(j+1)\exp[-2i\sigma(j+1)]}{1 + r(j)R(j+1)\exp[-2i\sigma(j+1)]} \quad (2)$$

for j=K, K−1, ... , 1,0, K being the number of layers in the stack.

Here, σ(j) are the complex coefficients showing both the attenuation and phase shift of light within the j-th layer, and r (j) is the reflectivity amplitude of each of the j layers, and are determined as follows:

$$r(j) = \frac{\sqrt{\varepsilon(j)} - \sqrt{\varepsilon(j+1)}}{\sqrt{\varepsilon(j)} - \sqrt{\varepsilon(j+1)}} \quad r(K+1) = 0$$

$$\sigma(j) = \frac{2\pi}{\lambda} d(j)\sqrt{\varepsilon(j)} \quad \sigma(K+1) = 0$$

$$\varepsilon(0) = \varepsilon_{superstrate} \quad \varepsilon(K+1) = \varepsilon_{substrate}$$

wherein d(j) is the thickness of the j-th layer, ∈(j) is the dielectric constant of the j-th layer for the corresponding wavelength λ.

The real part of the coefficient σ describes the phase shift, and the imaginary part the coefficient σ describes the attenuation coefficient. Index j=0 corresponds to the superstrate, and index j=K+1 corresponds to the substrate.

Function $\phi$=Phase(R) determines the phase of the complex reflectivity R (modulus 2π)

$$\text{Phase}(R) = \begin{cases} \theta & \text{for } \text{Re}(R) \geq 0 \text{ and } \text{Im}(R) \geq 0 \\ \theta + \pi & \text{for } \text{Re}(R) < 0 \text{ and } \text{Im}(R) \geq 0 \\ \theta & \text{for } \text{Re}(R) \geq 0 \text{ and } \text{Im}(R) < 0 \\ \theta - \pi & \text{for } \text{Re}(R) < 0 \text{ and } \text{Im}(R) < 0 \end{cases}$$

wherein $$\theta = \arctan\left(\frac{\text{Im}(R)}{\text{Re}(R)}\right)$$

and Re(R) and Im(R) are the real and imaginary parts of the complex reflectivity R, respectively.

In the case of one-dimensional grating (pattern), the phase $\phi_{UP} = \phi_{TE}$ for TE polarized light and $\phi_{UP} = \phi_{TM}$-polarized light. Phases $\phi_{TE}$ and $\phi_{TM}$ of the reflected electromagnetic wave for TE and TM polarized light are to be determined, as follows:

$$\phi_{TE} = \text{Phase}(R_{0,0}^{TE})$$

$$\phi_{TM} = \text{Phase}(R_{0,0}^{TM})$$

Here, the complex reflectivity matrixes $$R_{n,k}^{TE} \text{ and } R_{n,k}^{TM}$$

describes the reflectivity from the k-th incident diffraction order to the n-th reflected diffraction order for TE and TM polarizations, respectively. The components $R_{0,0}^{TE}$ and $R_{0,0}^{TM}$ correspond to the terms of the matrixes $R_{n,k}^{TE}$ and $R_{n,k}^{TM}$ with n=0 and k=0. The terms $R_{0,0}^{TE}$ and $R_{0,0}^{TM}$ describe the specula reflectivity of TE and TM polarized light, respectively. Matrixes $R_{n,k}^{TE}$ and $R_{n,k}^{TM}$ can be calculated by any rigorous electromagnetic approach. Matrixes $R_{n,k}^{TE}$ and $R_{n,k}^{TM}$ can be calculated using the known Rigorous Coupled Wave Approach (RCWA) formalism, the known Green Function Integral (GFI) formalism, or the known Rigorous Coupled Mode Theory (RCMT) formalism.

Step 2: Using the phase mapping (imaging) measured at the selected wavelength $\lambda$, the phase shift $\Delta\phi$ between the region of interest (Cu or W pad 11 in the case of metal CMP—FIG. 2A; or silicon dioxide pad 332 in the case of dielectric CMP—FIG. 2C), and the reference region (one of the sites 121, 132, 133 in the example of FIG. 2A; or site 331 in the example of FIG. 2C) is calculated.

Step 3: Dishing is now calculated using the following expression:

$$\text{Dishing} = \lambda \frac{\Delta\varphi - \varphi_{ROI} + \varphi_{UP}}{4\pi n}$$

wherein $\phi_{ROI}$ is the phase shift of light reflected from the Region Of Interest (ROI) pad (pad 11—Cu, W, or any other metal of interest in the case of metal CMP—FIG. 2A; or pad 332 of silicon dioxide pad in the case of dielectric CMP—FIG. 2C), and $\phi_{UP}$ is determined from equation (1) above; $\lambda$ is the selected wavelength of incident light; n is a refraction index of the ambient.

The phase shift $\phi_{ROI}$ of the reflected wave at the upper interface of the stack of interest can be calculated using equations (1) and (2). Depending on a specific application, spectrophotometric measurement may be required to extract the accurate parameters of a stack of interest.

EXAMPLE 2

Absolute Erosion Measurement as a Combination of Phase Mapping (Imaging) and Spectrophotometric Measurement In the present example, the optical monitoring system of FIG. 3B is applied to the structure of FIG. 2B and FIG. 2C.

Step 1: As indicated above, the spectrophotometric measurement allows extraction of data about the reference stack parameters, and using these stack parameters the phase $\phi_{UP}$ of the reflected wave at the upper interface of the reference stack can be calculated. Reference pad can be either in the upper layer (site 231 in FIG. 2B or site 332 in FIG. 2C) or in the underneath layers (sites 232 and 233 in FIG. 2B). The spectrophotometric measurement is done in the site of interest (for metal CMP this is a pad in the form of spaced-apart metal-containing regions in the erosion measurement applications, which it pad 21 in the example of FIG. 2B; for dielectric CMP this is a pad in the form of spaced-apart different dielectric regions, which are silicon dioxide and silicon nitride, in pad 333 of FIG. 2C), and point 331 in the example of FIG. 2C, or one of the following sites (points) in the example of FIG. 2B: point 221 (for stack 231), point 222 (for stack 232), point 223 (for stack 233), and point 124 (for stack 134). The so-measured spectrum is analyzed and the parameters of the respective stack are determined. Using the calculated parameters, the phase shift of the reflected wave $\phi_{UP}$ at the upper interface is calculated for a selected wavelength $\lambda$.

Step 2: Using the phase mapping (imaging) measured at the selected wavelength $\lambda$, the phase shift $\Delta\phi$ between the region of interest (21 in FIG. 2B or 333 in FIG. 2C) and the reference region (one of the reference stacks) is calculated.

Step 3: Erosion is calculated using the following expression:

$$\text{Erosion} = \lambda \frac{\Delta\varphi + \varphi_{Pattern} - \varphi_{UP}}{4\pi n}$$

wherein $\phi_{Pattern}$ is the phase shift of light reflected from the pattern of interest 21 or 333. The pattern phase shift $\phi_{Pattern}$ has to be calculated for the TE, TM, or other polarization, depending on the polarization of light used for the phase mapping.

In the case of one-dimensional grating (pattern), the phase $\phi_{Pattern}=\phi_{TE}$ for TE polarized light and $\phi_{Pattern}=\phi_{TM}$ for TM—polarized light. Phases $\phi_{TE}$ and $\phi_{TM}$ of the reflected electromagnetic wave for TE and TM polarized light can be determined, as follows:

$\varphi_{TE} = \text{Phase}(R_{0,0}^{TE})$ $\varphi_{TM} = \text{Phase}(R_{0,0}^{TM})$ Here, the complex reflectivity matrixes $R_{n,k}^{TE}$ and $R_{n,k}^{TM}$ describes the reflectivity from the k-th incident diffraction order to the n-th reflected diffraction order for TE and TM polarizations, respectively. The components $R_{0,0}^{TE}$ and $R_{0,0}^{TM}$ correspond to the terms of the matrixes $R_{n,k}^{TE}$ and $R_{n,k}^{TM}$ with n=0 and k=0. The terms $R_{0,0}^{TE}$ and $R_{0,0}^{TM}$ describe the specula reflectivity of TE and TM polarized light, respectively. Matrixes $R_{n,k}^{TE}$ and $R_{n,k}^{TM}$ can be calculated by any rigorous electromagnetic approach. Matrixes $R_{n,k}^{TE}$ and $R_{n,k}^{TM}$ can be calculated using the known Rigorous Coupled Wave Approach (RCWA) formalism, the known Green Function Integral (GHI) formalism, or the known Rigorous Coupled Mode Theory (RCMT) formalism.

The pattern 21 (or 333) should have small pitch and/or large metal duty cycle (DC) values. In his case, the pattern 21 is essentially opaque and the phase $\phi_{PATTERN}$ practically does not depend or is fully independent on the parameters (thickness) of the underneath layers, and can be calculated from the DC and pitch of the pattern. The phase $\phi_{Pattern}$ can also be calibrated/measured by a comparison of the obtained results to reference data obtained with a reference tool for example the HRP-340 high-resolution contact surface profiler commercially available from KLA-Tencor. In this case, the dishing or erosion of the same object is measured by both reference tool and phase imaging technique. The dishing or erosion measured by reference tool is denoted as $h_1$. The dishing ox erosion measured by phase imaging technique is denoted as $h_2$. The calibrated value of phase shift $\phi'_{Pattern}$ has the form $$\varphi'_{Pattern} = \varphi_{Pattern} - \frac{4\pi n(h_1 - h_2)}{\lambda}.$$

A pattern with a large duty cycle (DC>0.5) and/or small pitch (Pitch<$\lambda$), works as an effective substrate that isolates TE and/or TM polarization from penetrating through the pattern into underneath layer(s). For example, in the case of Cu, a patterned area with a pitch of 0.6 um and DC=0.8 is opaque for the TE polarization for $\lambda$>600 nm. Another example in the case of Cu is a patterned pad with a pitch of 0.3 um and DC=0.5. This pattern is opaque for the TM polarization for $\lambda$>500 nm. Hence, the phase mapping (imaging) and/or spectrophotometric measurement on patterned areas is preferably taken with specific polarization TE or TM, although for some cases (small pitch and dense pattern) unpolarized light can also be used.

EXAMPLE 3

Absolute Dishing Measurement Using Phase Mapping (Imaging) Only

For these measurements, the optical system of FIG. 3A is used.

Step 1: This measurement, scheme includes measurement of the phase difference $\Delta\phi$ on the pad of interest and the reference pad (Cu or W), wherein the reference pad is small enough (from 2x2 um$^2$ to 10x10 um$^2$), i.e., has negligible dishing effect as compared to the pad of interest. In this case, the phase shift of the reflected light is the same on the reference pad and the pad of interest due to the substantially fill reflection, of incident light by the reference pad and pad of interest in the upper layer.

Step 2: Dishing is calculated according to the following expression:

$$\text{Dishing} = \lambda \frac{\Delta\varphi}{4\pi n}.$$

The reference pad can be of an arbitrary shape (square, line, etc.). To improve the accuracy the metal recess effect can also be taken into account.

EXAMPLE 4

Absolute Erosion Measurement Using Phase Mapping (Imaging) Only

Here, the optical system of FIG. 3A is used.

Step 1: This measurement scheme includes measurement of the phase difference $\Delta\phi$ on the pattern of interest and reference, wherein the reference pad is small enough (from 2x2 um$^2$ to 10x10 um$^2$), i.e., has negligible dishing effect as compared to that of the pad (pattern) of interest.

Step 2: Erosion is calculated according to the following expression:

$$\text{Erosion} = \lambda \frac{\Delta\varphi - \varphi_{Pattern} + \varphi_{ROI}}{4\pi n}$$

wherein $\phi_{Pattern}$ is the phase shift of light reflected from the pattern of interest.

The pattern phase shift $\phi_{Pattern}$ has to be calculated for the TE, TM, or other polarization depending on the polarization of light used for the phase mapping.

The pattern of interest should have small pitch and/or large DC values. In his case, the pattern is essentially opaque and the phase $\phi_{Pattern}$ practically does not depend or is fully independent on the parameters (thickness) of the underneath layers and can be calculated from DC. The phase $\phi_{Pattern}$ can also be calibrated/measured by a comparison of the obtained results to a reference tool, for example the HRP-340 high-resolution contact surface profiler commercially available from KLA-Tencor. In this case, the dishing or erosion of the same object is measured by both the reference tool and the phase imaging technique. The dishing or erosion measured by the reference tool is denoted as $h_1$. The dishing or erosion measured by the phase imaging system is denoted as $h_2$. The calibrated value of the phase shift $\phi'_{Pattern}$ has the form $\varphi'_{Pattern} = \varphi_{Pattern} - \frac{4\pi n(h_1 - h_2)}{\lambda}.$ A pattern with a large duty cycle (DC>0.5) and/or small pitch (Pitch<$\lambda$) works as an effective substrate, which isolates TE and/or TM polarization from penetrating through the pattern into the underneath layer(s). For example, in the case of Cu, a patterned area with a pitch of 0.6 um and DC=0.8 is opaque for the TE polarization for $\lambda$>600 nm. Another example in the case of Cu is a patterned pad with a pitch of 0.3 um and DC=0.5. This pattern is opaque for the TM polarization for $\lambda$>500 nm. The phase mapping (imaging) on patterned areas is thus preferably taken with specific polarization TE or TM, although for some cases (small pitch and dense pattern) unpolarized light can also be used.

The reference pad can be of an arbitrary shape (square, line, etc.). To improve the accuracy the metal recess effect can also be taken into account.

Additionally, a phase difference between two different patterned areas may be used for absolute erosion measurements, as follows:

Step A: Measurement of the phase difference $\Delta\phi$ is applied to the patterned area of interest and a similarly patterned reference area, wherein the reference area is small enough (from 2×2 um² to 10×10 um²), that it has no erosion effect. In this case, the phase shift of the reflected light is the same on the reference area and the area of interest.

Step B: Erosion is calculated according to the following expression:

$$\text{Erosion} = \lambda \frac{\Delta\varphi}{4\pi n}$$

The reference area can be of an arbitrary shape (square, fine, etc.).

EXAMPLE 5

Figure 4A:
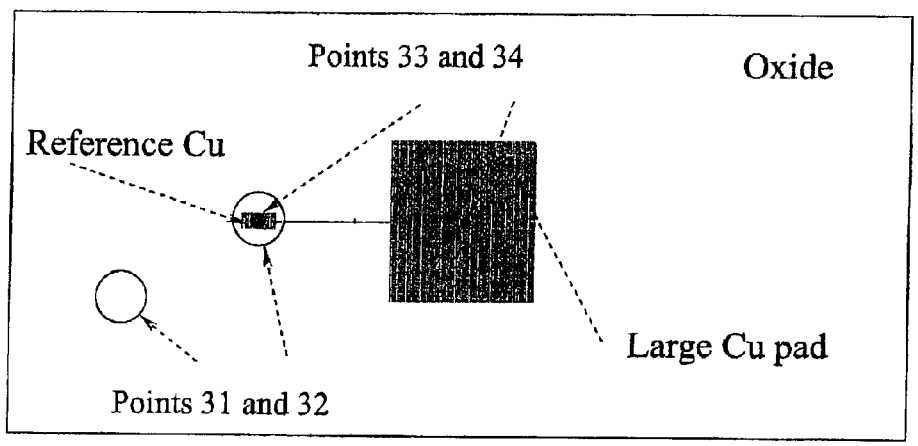
FIGS. 4A and 4B illustrate, respectively, the top view of a large Cu pad and a reference pad, and the same but using a part of a test structure as a reference pad, used in one specific example of a method according to the invention for a global "dishing induced" non-planarity measurement as a combination of phase mapping and spectrophotometric measurement.

Global "Dishing Induced" Non-planarity Measurement as a Combination of Phase Mapping (Imaging) and Spectrophotometric Measurement The suggested scheme measures global non-planarity that originates from dishing. Now reference is made to FIGS. 4A and 4B, which illustrate, respectively, the top view of a large Cu pad and a reference pad, and the same but using a part of a test structure as a reference pad.

Step 1: A spectrophotometric measurement applied to a first point 31 (oxide layer), preferably far away from the large Cu pad, gives a cumulative Oxide thickness $H_1$.

Step 2: A spectrophotometric measurement applied to a second point 32 (within the oxide region) on the small reference Cu pad (from 2×2 um² to 15×15 um²; or 2 to 15 um copper line) gives a cumulative Oxide thickness $H_2$ near the Cu surface.

Step 3: A measurement of the phase difference $\Delta\phi$ between the pad of interest (large Cu pad) and the reference pad (from a third point 33 to a fourth point 34 of FIGS. 4A and 4B) is carried using the phase mapping.

Step 4: Dishing is calculated as follows:

$$\text{Dishing} = H_1 - H_2 + \lambda \frac{\Delta\varphi}{4\pi n}$$

Figure 4B:
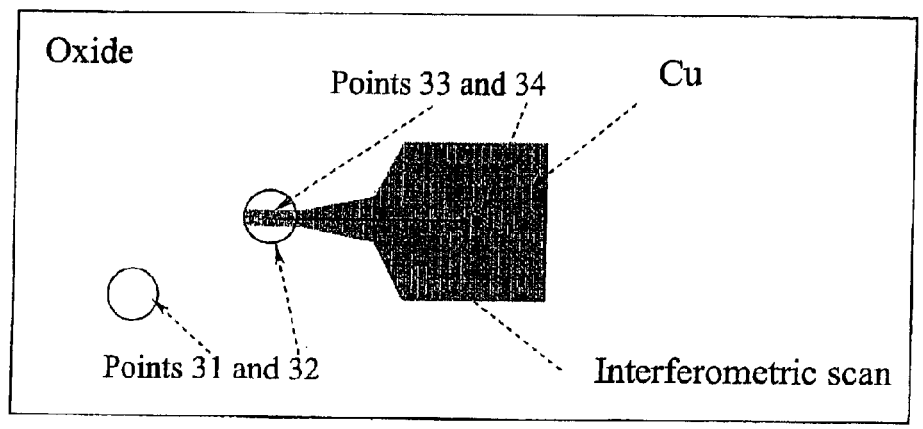

Using the test structure of FIG. 4B, allows measuring of a large dishing without order skips. It happens because the phase changes along the line from point 33 to point 34 can be unwrapped.

Figure 5:
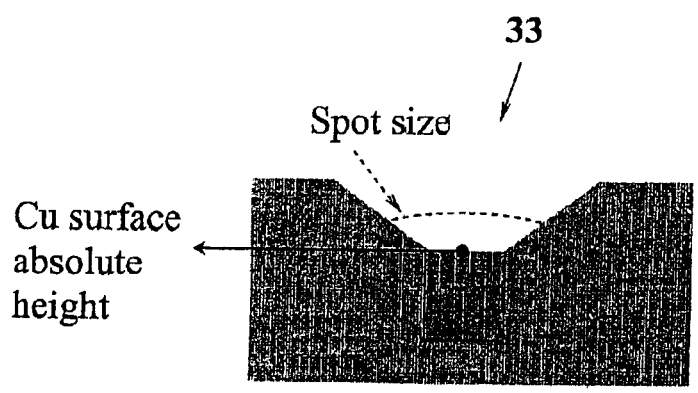
FIG. 5 more specifically illustrates the section view of a measurement point in the structure in the example of FIGS. 4A and 4B.

FIG. 5 more specifically illustrates the section view of the measurement point 33. By applying spectrophotometric measurements (e.g., based on the technique disclosed in the above-mentioned US patents) to the point 33, the absolute height of the Cu surface is measured.

EXAMPLE 6

Figure 6:
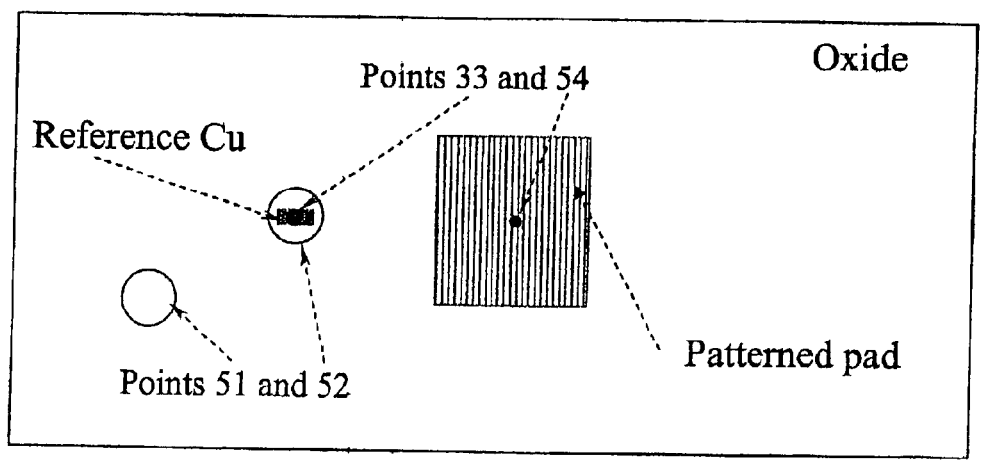
FIG. 6 schematically illustrates the top view of a patterned pad and a reference pad of the structure used in another specific example of a method according to the invention for a global "erosion induced" non-planarity measurement as a combination of phase mapping and spectrophotometric measurement

Global "Erosion Induced" Non-planarity Measurement as a Combination of Phase Mapping (Imaging) and Spectrophotometric Measurement In this example, the optical system of FIG. 3B is used. The suggested scheme, aimed at measuring the global non-planarity that originates from erosion, will be described with reference to FIG. 6 schematically illustrating the top view of a patterned pad and a reference pad.

Step 1: A spectrophotometric measurement is applied to a first point 51 (far away from the patterned pad), which gives a cumulative Oxide thickness $H_1$.

Step 2: A spectrophotometric measurement is applied to a second point 52 on the small reference (Cu) pad (from; 2×2 um² to 15×15 um²; or 2 to 15 um copper line), which gives a cumulative Oxide thickness $H_2$ near the Cu surface.

Step 3: The phase difference $\Delta\phi$ between the pad of interest (patterned pad) and the reference pad (from a third point 33 to a fourth point 54) is measured.

Step 4: Erosion is calculated as follows:

$$\text{Erosion} = H_1 - H_2 + \lambda \frac{\Delta\varphi - \varphi_{Pattern} + \varphi_{ROI}}{4\pi n}$$

wherein $\phi_{Pattern}$ is the phase shift of light reflected from the pattern of interest.

The pattern phase shift $\phi_{Pattern}$ has to be calculated for the TE, TM, or other polarization depending on the polarization of light used for the phase mapping.

This pattern should have small pitch and/or large DC values. In this case, the pattern is essentially opaque and the phase $\phi_{Pattern}$ does not depend (or practically does not depend) on the thickness of the previous layers and can be calculated from DC. The phase $\phi_{Pattern}$ can also be calibrated/measured by a comparison of the obtained results to a reference tool (surface profiler).

Pattern with a large duty cycle (DC>0.5) and/or a small pitch (Pitch<$\lambda$) works as an effective substrate, which isolates TE and/or TM polarization from penetrating below the pattern. For example, in the case of Cu, a patterned area with a pitch of 0.6 um and DC=0.8, is opaque for the TE polarization for $\lambda$>600 nm. Another example in the case of Cu is a patterned pad with a pitch of 0.3 um and DC=0.5. This pattern is opaque for the TM polarization for $\lambda$>500 nm. It means that the phase mapping (imaging) on patterned areas is preferably taken with specific polarization TE or TM, although for some cases (small pitch and dense pattern) unpolarized light can also be used. The reference pad can be of an arbitrary shape (square, line, etc.). To improve the accuracy, the metal recess effect can also be taken into account.

EXAMPLE 7

Relative Dishing-to-dishing Measurement Using Phase Mapping (Imaging) Only

Dishing depends on both the pad size (usually the larger the pad the larger the dishing size) and the pad's environment (e.g., in-die versus in-scribe location, etc.). The CMP process can be monitored by measuring a $\Delta DD$ characteristic, which, is a difference of the dishing between small and large pads, or in-die versus in-scribe location. This difference correlates with the absolute value of the dishing itself. This correlation can be taken into account using correction formula. On the other hand, his difference $\Delta DD$ itself is an important parameter for the CMP process monitoring.

Step 1: Using the phase map obtained with the system of FIG. 3A, the phase difference $\Delta\phi$ between two pads is measured.

$$\text{Step 2: } \Delta DD = \lambda \frac{\Delta\varphi}{4\pi n}$$

It should be noted, that for the purpose of the process control, the phase difference $\Delta\phi$ between more than two pads of different sizes can be used. In this case, the phase vs. pad's size may be calculated and analyzed, and correlation between the pad's size and the dishing effect thereon can further be used for the CMP process control.

EXAMPLE 8

Relative Erosion-to-dishing Measurement Using Phase Mapping (Imaging) Only

Dishing and erosion effects behave differently under different CMP polish conditions (pressure, polish time, temperature, slurry/chemistry variation, etc.). Usually, erosion is less than dishing. CMP process can be monitored, by measuring the ΔED characteristic, which is the difference between the dishing and erosion of different pads. This difference correlates with the absolute value of dishing and erosion. This correlation can be taken into account using correction formula. On the other hand, this difference ΔED itself is an important parameter for CMP process monitoring.

Step 1: Using the phase map, the phase difference Δϕ between two pads is measured.

$$\text{Step 2: } \Delta ED = \lambda \frac{\Delta \varphi - \varphi_{Pattern} + \varphi_{ROI}}{4\pi n}$$

where $\phi_{Pattern}$ is the phase shift of light reflected from the pattern of interest. The pattern phase shift $\phi_{Pattern}$ has to be calculated for the TE, TM, or other polarization depending on the polarization of light used for the phase mapping.

This pattern should have small pitch and/or large DC values. In this case the pattern is essentially opaque and phase $\phi_{Pattern}$ doesn't depend (or practically doesn't depend) on the parameters (thickness) of the underneath layers and can be calculated from DC. The phase $\phi_{Pattern}$ can also be calibrated/measured by comparing the obtained results to a reference tool (surface profiler). Pattern with large duty cycle (DC>0.5) and/or small pitch (Pitch<λ) works as an effective substrate, which isolates TE and/or TM polarization from penetrating below the pattern. For example, in the case of Cu, patterned area with pitch 0.6 um and DC=0.8, is opaque for TE polarization for λ>600 nm. Another example in the case of Cu is a patterned pad with pitch 0.3 um and DC=0.5, this pattern is opaque for TM polarization for λ>500 nm. Hence, the phase mapping (imaging) on patterned areas is preferably taken with specific polarization TE or TM, although for some cases (small pitch and dense pattern) unpolarized light can also be used.

EXAMPLE 9

Relative Erosion-to-erosion Measurement Using Phase Mapping (Imaging) Only

Erosion for pattern sites with different pitches and/or duty cycles behaves differently under different CMP polish conditions (pressure, polish time, temperature, slurry/chemistry, variation, etc.). CMP process can be monitored by measuring the ΔEE characteristic, i.e., a difference between the erosion on pads with different pitch and/or duty cycles, or in-die versus in-scribe-line location. This difference correlates to the absolute value of the erosion effect. This correlation can be taken into account using correction formula. On the other hand, this difference ΔEE itself is an important parameter for CMP process monitoring.

It should be noted, that for the process control purposes, a phase difference Δϕ between more than two patterned sites with the same pitch and DC but different area size can be used. In this case, phase vs. area size may be calculated and analyzed, and correlation between pad's size and erosion effect thereon can be further used for CMP process control.

Step 1: Using phase map the phase difference Δϕ between two patterns is measured.

$$\text{Step 2: } \Delta EE = \lambda \frac{\Delta \varphi - \varphi_{Pattern2} + \varphi_{Pattern1}}{4\pi n}$$

wherein $\phi_{Pattern1}$ and $\phi_{Pattern2}$ are the phase shifts of light reflected from the pattern on two different sites, respectively.

The patterns phase shifts $\phi_{Pattern1}$ and $\phi_{Pattern2}$ have to be calculated for the TE, TM, or other polarization depending on polarization of the light, which is used for the phase mapping.

These patterns should have small pitch and/or large DC values. In this case, the pattern is essentially opaque and the phases $\phi_{Pattern1}$ and $\phi_{Pattern2}$ do not depend (or practically do not depend) on the parameters (thickness) of the underneath layer(s) and can be calculated from DC. The phases $\phi_{Pattern1}$ and $\phi_{Pattern2}$ can also be calibrated/measured by comparing the obtained results to the reference tool (surface profiler). A pattern with large duty cycle (DC>0.5) and/or small pitch (Pitch<λ) works as an effective substrate, which isolates TE and/or TM polarization from penetrating below the pattern. For example, in the case of Cu, patterned area with pitch 0.6 um and DC=0.8, is opaque for TE polarization for λ>600 nm. Another example in the case of Cu is a patterned pad with pitch 0.3 um and DC=0.5, this pattern is opaque for TM polarization for λ>500 nm. It means that the phase mapping (imaging) on patterned areas is preferably taken with specific polarization TE or TM, although for some cases (small pitch and dense pattern) unpolarized light can also be used.

EXAMPLE 10

Residue Measurement as a Combination of Phase Mapping (Imaging) and Spectrophotometric Measurement Step 1: Spectrophotometric measurement allows determining the parameters of the stack and presence of residues.

Step 2: Since the phase variation is much more sensitive to the presence of residues than the amplitude variation, the phase variation could be used for the verification of preliminary spectrophotometric measurement. The phases of light reflected from regions with and without residues (i.e., regions with different thickness) are compared with the measured phase map. In this case, the dishing or erosion of the same object is measured by both the reference tool and the phase imaging technique. The dishing or erosion measured by the reference tool is denoted as $h_1$. The dishing or erosion measured by phase imaging technique is denoted as $h_2$. The calibrated value of phase shift $\phi'_{Pattern}$ has the form $$\varphi'_{Pattern} = \varphi_{Pattern} - \frac{4\pi n(h_1 - h_2)}{\lambda}.$$

This comparison allows for determining the residue thickness.

EXAMPLE 11

Residue Detection Using the Phase Mapping (Imaging) Only

Step 1: A "golden" phase map is measured from a wafer without residue.

Step 2: A phase variation is much more sensitive to the presence of the residues than the amplitude variation. The phase map of the wafer of interest is measured and compared with the "golden" map. A constant offset between the "golden" and measured phase map is calculated and subtracted from the measured phase map. The so-obtained normalized phase map is compared to the "golden" one. A difference between the "golden" and normalized phase maps is indicative of the presence of residues.

EXAMPLE 12

Defect and Corrosion Detection Using the Phase Mapping (Imaging) Only

Step 1: A "golden" phase map is measured from a wafer without defect and corrosion.

Step 2: The phase map of a wafer of interest is measured and compared with the "golden" map. A constant offset between the "golden" and measured phase maps is calculated and subtracted from the measured phase map. The so-obtained normalized phase map is compared to the "golden" one. A difference between the "golden" and normalized phase maps is thus indicative of the presence of defects or corrosion.

Additionally, a calibration of the phase map may be performed, mainly for the wafer's tilt correction. To this end, the phase signals from at least three similar or identical features (preferably small pads) located in a non-collinear manner on the wafer's surface (forming a triangle) are used. Supposing that the elevation at these features is identical, the phase difference therebetween is indicative of the wafer's tilt and may be used for the tilt correction.

Those skilled in the art will readily appreciate that many modifications and changes may be applied to the invention as hereinbefore exemplified without departing from its scope, as defined in and by the appended claims.

What is claimed is:

1. A method for use in controlling a process of material removal from the surface of a patterned structure, by measuring at least one of residue, erosion, dishing and corrosion effects in the structure, the method comprising:

imaging the structure utilizing phase modulation of light reflected from the structure, thereby obtaining a phase map of the structure;

analyzing said phase map while utilizing data indicative of light reflective properties of layer stacks of the structure to determine a phase difference between light reflected from a selected site in the structure and at least one reference site in the structure spaced-apart from said selected site, said phase difference being indicative of the measured effect in at least the selected site.

2. The method according to claim 1, wherein said phase difference is informative of a relative value of the measured effect in said selective site as compared to that of said at least one reference site.

3. The method according to claim 1, wherein the phase difference is substantially independent on the reflective properties of the layer stacks within the measured sites of the structure.

4. The method according to claim 1, wherein said at least one reference site has a relatively small value of the measured effect as compared to that of the selected site, said phase difference being informative of an absolute value of the measured effect in the selected site.

5. The method according to claim 1, comprising applying spectrophotometric measurements to at least one reference site of the structure to obtain data indicative of the intensity of light reflected from said at least one reference site as a function of wavelength, thereby determining an effect of the light reflective properties of the structure onto said phase difference, and enabling determination of an absolute value of the measured effect.

6. The method according to claim 5, comprising applying spectrophotometric measurements to the selected site of the structure.

7. The method according to claim 5, wherein said at least one reference site has a relatively small value of the measured effect.

8. The method according to claim 5, wherein the spectrophotometric measurements comprise illuminating the structure with polarized light.

9. The method according to claim 2, comprising utilizing the determined phase difference $\Delta\phi$ between the two selected and reference sites to determine a difference $\Delta DD$ of the dishing effects in these sites according to the following equation:

$$\Delta DD = \lambda \frac{\Delta\varphi}{4\pi n},$$

wherein n is a refraction index of the ambient.

10. The method according to claim 9, comprising determining an absolute value of the dishing effect in the selected site utilizing correlation between the difference $\Delta DD$ and an absolute value of the dishing effect.

11. The method according to claim 2, comprising utilizing the phase map and the phase difference $\Delta\phi$ between the non-patterned selected site and the patterned reference site to determine a difference $\Delta ED$ between the dishing and erosion effects in these sites according to the following equation $$\Delta ED = \lambda \frac{\Delta\varphi - \varphi_{Pattern} + \varphi_{ROI}}{4\pi n}$$

wherein $\phi_{Pattern}$ is the phase shift of light reflected from the patterned reference site, and $\phi_{ROI}$ is the phase shift of light reflected from the selected non-patterned site.

12. The method according to claim 11, comprising determining an absolute value of at least one of the dishing and erosion effects in at least one the selected and reference sites utilizing correlation between the difference $\Delta ED$ and an absolute value of one of the dishing and erosion effects.

13. The method according to claim 11, wherein the pattern in the measured reference site is characterized by at least one of small pitch and large duty cycle (DC) values, the pattern being thereby substantially opaque, and the phase $\phi_{Pattern}$ being therefore substantially independent on the reflective properties of the layer stack in said reference site and being determined by the DC value.

14. The method according to claim 11, wherein the imaging comprises illumination of the structure with polarized light.

15. The method according to claim 2, comprising utilizing the phase map and the phase difference $\Delta\phi$ between the selected patterned site and the reference patterned site to determine a difference $\Delta EE$ between the erosion effects in these two sites, according to the following equation:

$$\Delta EE = \lambda \frac{\Delta\varphi - \varphi_{Pattern2} + \varphi_{Pattern1}}{4\pi n}$$

wherein $\phi_{Pattern1}$ and $\phi_{Pattern2}$ are the phase shifts of light reflected from the patterns on the two sites, respectively.

16. The method according to claim 15, comprising determining an absolute value of the erosion effect in the selected site utilizing correlation between the difference $\Delta EE$ and an absolute value of the erosion effect.

17. The method according to claim 15, wherein the patterns in the selected and reference sites differ from each other in at least one of pitch and duty cycle (DC) values.

18. The method according to claim 17, wherein each of the patterns in the selected and reference sites is characterized by at least one of the small pitch and large DC values, the patterns being thereby substantially opaque, and the phases $\phi_{Pattern1}$ and $\phi_{Pattern2}$ being therefore substantially independent on the reflectivity properties of the layer stacks in said sites and being determined by the DC values.

19. The method according to claim 15, wherein the imaging comprises illumination of the structure with polarized light.

20. The method according to claim 1, comprising:
providing a phase map of a golden structure, said golden structure being constructed similar to the measured structure, but having no corrosion effect;
comparing the phase maps of the golden and measured structure to calculate a constant offset between said phase maps and subtract the calculated offset from the measured phase map, to thereby obtain a normalized phase map;
comparing the normalized phase to the golden phase map to determine a difference between them, said difference being indicative of the presence of defects or corrosion effect in the structure.

21. The method according to claim 1, comprising:
providing a phase map of a golden structure, said golden structure being constructed similar to the measured structure, but having no residue effect,
comparing the phase maps of the golden and measured structure to calculate a constant offset between said phase maps and subtract the calculated offset from the measured phase map, to thereby obtain a normalized phase map;
comparing the normalized phase to the golden phase map to determine a difference between them, said difference being indicative of the presence of the residue effect in the structure.

22. The method according to claim 4, comprising utilizing the determined phase difference $\Delta\phi$ between the selected and reference sites to calculate the absolute value of the dishing effect as follows:

$$\text{Dishing} = \lambda \frac{\Delta\varphi}{4\pi n}$$

wherein n is a refraction index of the ambient.

23. The method according to claim 4, comprising utilizing the determined phase difference $\Delta\phi$ between the selected site and the reference site to calculate the absolute value of the erosion effect in the selected site as follows:

$$\text{Erosion} = \lambda \frac{\Delta\varphi - \varphi_{Pattern} + \varphi_{ROI}}{4\pi n}$$

wherein $\phi_{Pattern}$ is the phase shift of light reflected from the pattern in said reference site; $\phi_{ROI}$ is the phase shift of light reflected from the pattern in said selected site; and n is a refraction index of the ambient.

24. The method according to claim 23, wherein the pattern in said reference site is characterized by at least one of small pitch value and a high duty cycle (DC) value, the phase $\phi_{Pattern}$ thereby being substantially independent on the reflectivity properties of the layer stacks in the respective site, and is determined by the DC value.

25. The method according to claim 23, wherein the imaging is carried out with polarized light.

26. The method according to claim 4, comprising determining the phase difference between the light reflected from the selected and reference sites with similar patterns, and calculating a value of the erosion effect in the selected site according to the following expression:

$$\text{Erosion} = \lambda \frac{\Delta\varphi}{4\pi n}$$

wherein n is a refraction index of the ambient.

27. The method according to claim 5, comprising determining a value of the dishing effect according to the following expression:

$$\text{Dishing} = \lambda \frac{\Delta\varphi - \varphi_{ROI} + \varphi_{UP}}{4\pi n}$$

wherein $\phi_{ROI}$ is the phase shift of the light reflected from said selected site, and $\phi_{UP}$ is the phase shift of the light reflected from the reference site and is determined as $\phi_{UP}$=Phase(R), wherein R is the total reflection from the structure obtained in the spectrophotometric measurements, $\lambda$ is the selected wavelength of incident light, which is that used for the phase mapping; and n is a refraction index of the ambient.

28. The method according to claim 5, comprising determining a value of the erosion effect according to the following expression:

$$\text{Erosion} = \lambda \frac{\Delta\varphi - \varphi_{Pattern} + \varphi_{UP}}{4\pi n}$$

wherein $\phi_{Pattern}$ is the phase shift of light reflected from the pattern in said selected site, and $\phi_{UP}$ is the phase shift of the light reflected from the reference site and is determined as $\phi_{UP}$=Phase®, wherein R is the total reflection from the structure obtained in the spectrophotometric measurements, $\lambda$ is the selected wavelength of incident light, which is that used for the phase mapping; and n is a refraction index of the ambient.

29. The method according to claim 28, wherein the pattern in said selected site is characterized by at least one of a small pitch value and a high value of a metal duty cycle (DC), said pattern being therefore substantially opaque and the phase $\phi_{Pattern}$ being substantially independent on the parameters the layer stack, and being determined from the DC and pitch values of the pattern.

30. The method according to claim 28, wherein the imaging is carried out with polarized incident light.

31. The method according to claim 8, comprising:
using the spectrophotometric measurements to determine a thickness $H_1$ of a substantially transparent layer in one reference site of the structure spaced from said selected site, and to determine a thickness $H_2$ of a substantially transparent layer adjacent to an upper layer of the stricture within another reference site;
utilizing the determined phase difference $\Delta\phi$ between the selected site and one of said reference sites to determine a value of the dishing effect in the selected site as follows $$\text{Dishing} = H_1 - H_2 + \lambda \frac{\Delta\varphi}{4\pi n}.$$

32. The method according to claim 8, comprising:
using the spectrophotometric measurements to determine a thickness $H_1$ of a substantially transparent layer in one reference site of the structure spaced from the selected site, and to determine a thickness $H_2$ of a substantially transparent layer adjacent to an upper layer of the structure within another reference site;
utilizing the determined phase difference $\Delta\phi$ between the selected patterned site and one of said reference sites to determine a value of the erosion effect in the selected site as follows:

$$\text{Erosion} = H_1 - H_2 + \lambda \frac{\Delta\varphi - \varphi_{Pattern} + \varphi_{Metal}}{4\pi n}$$

wherein $\phi_{Pattern}$ is the phase shift of light reflected from said selected site, and $\phi_{Metal}$ is the phase shift of light reflected from said one of the reference sites.

33. The method according to claim 32, wherein the pattern in said selected site is characterized by at least one of a small pitch value and a high value of a metal duty cycle (DC), said pattern being therefore substantially opaque and the phase $\phi_{Pattern}$ being substantially independent on the parameters the layer stack, and being determined from the DC value of the pattern.

34. The method according to claim 32, wherein the imaging is carried out with polarized incident light.

35. The method according to claim 1, comprising calibration of the phase map, thereby enabling correction of the determined value of said at least one effect for the structure's tilt relative to an optical measurement system.

36. The method according to claim 35, wherein said calibration comprises selecting from the phase map signals corresponding to at least three sites of the structure having substantially identical properties with respect to at least one of said effects and located in a non-collinear manner on the structure's surface, the phase difference between said signals being indicative of the structure's tilt.

37. The method according to claim 1, for use in controlling a process of Chemical Mechanical Planarization applied to said structure.

38. The method according to claim 5, wherein for determining the erosion effect, the phase shift is calculated by using rigorous electromagnetic approaches for solving the Maxwell equations.

39. The method according to claim 38, wherein said rigorous electromagnetic approach includes one of the following: Rigorous Coupled Wave Approach (RCWA), Green Function Integral (GFI) approach, Rigorous Coupled Mode Theory (RCMT).

40. A method for use in controlling a process of material removal from the surface of a patterned structure, by measuring at least one of residue, erosion, dishing and corrosion effects in the structure, the method comprising:

imaging the structure utilizing phase modulation of light reflected from the structure, thereby obtaining a phase map of the structure;

applying spectrophotometric measurements to at least one reference site of the structure spaced-apart from a selected site of the structure, thereby obtaining measured data indicative of the intensities of light reflected from the at least one reference site of the structure as a function of wavelength of incident light properties of a layer stack of the structure in said at least one reference site;

analyzing said phase map to determine a phase difference between light reflected from different sites of the structure, and analyzing said measured data to determine an effect of the reflective properties of a layer stack in said at least one reference site onto said phase difference at the wavelength used for the phase mapping, and thereby determine an absolute value of the measured effect in at least the selected site of the structure.

41. An optical system for use in controlling a process of material removal from the surface of a patterned structure, to determine at least one of residue, erosion, dishing and corrosion effects in the structure, the system comprising:

an imaging system having an illuminator unit, a detector unit, and a light directing arrangement for directing incident light to the structure and directing light reflected from the structure to the detector unit, the light directing arrangement comprising a phase modulator accommodated in optical path of the reflected light propagating to the detector, an output of the detector being in the form of at least one intensity map; and a control unit connectable to the imaging system and operable to receive the output of the detector and process it to obtain data indicative of a phase map of the structure, the control unit having a data processing and analyzing utility operating to analyze the phase map to determine at least one of the following:

the value of at least one of the erosion and dishing effects in a selected site of the structure, determined by a phase difference between the selected site and a reference site of the structure spaced-apart from said selected site, wherein said reference site has a relatively small value of the measured effect as compared to that of the selected site;

a difference $\Delta DD$ of the dishing effects between a selected site of the structure and a relatively small reference site of the structure spaced-apart from the selected site;

an absolute value of the dishing effect in the selected site which is relatively large as compared to a reference site of the structure spaced-apart from the selected site, by utilizing correlation between the difference $\Delta DD$ and an absolute value of the dishing effect;

a difference $\Delta ED$ between the dishing and erosion effects in a selected site of the structure and a reference site of the structure spaced-apart from the selected site;

absolute values of the dishing and erosion effects in the selected and reference sites, by utilizing correlation between the difference $\Delta ED$ and absolute value of the dishing and erosion effects;

a difference of the erosion effects between a selected patterned site of the structure and a relatively small, reference patterned site of the structure;

a difference $\Delta EE$ between the erosion effects in a selected site of the structure and a reference site spaced-apart from the selected site; an absolute value of the erosion effect in said selected site utilizing correlation between the difference $\Delta EE$ and an absolute value of the erosion effect;

presence of defects or corrosion effect in the structure;

presence of residue effect in the structure.

42. The system according to claim 41, comprising a spectrophotometer system, said control unit operating to receive an output of the spectrophotometer and process said output to determine an absolute value of the at least one of said effects in at least the selected site of the structure.

43. An optical system for use in controlling a process of material removal from the surface of a patterned structure, to determine at least one of residue, erosion, dishing and corrosion effects in the structure, the system comprising:

an imaging system having an illuminator unit, a detector unit, and a light directing arrangement for directing incident light to the structure and directing light reflected from the structure to the detector unit, the light directing arrangement comprising a phase modulator accommodated in optical path of the reflected light propagating to the detector, an output of the detector being in the form of at least one intensity map;

a spectrophotometer system operable for applying spectrophotometric measurements to at least one reference site of the structure spaced-apart from a selected site of the structure and thereby obtaining output in the form of intensities of light reflected from the at least one reference site of the structure as a function of wavelength of incident light; and a control unit connectable to the imaging system and to the spectrophotometer system, and operable to receive the output of these systems and process them to obtain data indicative of a phase map of the structure and data indicative of the reflective properties of a layer stack of the structure in the at least one reference site, the control unit having a data processing and analyzing utility operating to determine at least one of the following:

an absolute value of the dishing effect in the selected site;

an absolute value of the erosion effect in the selected site having the pattern characterized by at least one of a small pitch and a large metal duty cycle (DC) value;

a difference $\Delta DD$ of the dishing effects between the selected site and the relatively small reference site;

an absolute value of the dishing effect in the selected site, by utilizing correlation between the difference $\Delta DD$ and an absolute value of the dishing effect;

a difference $\Delta ED$ between the dishing and erosion effects in the selected and reference sites;

an absolute value of one of the dishing and erosion effects utilizing correlation between the difference $\Delta ED$ and an absolute value of one of the dishing and erosion effects;

a difference $\Delta EE$ between the erosion effects in the selected and reference sites of the structure;

absolute values of the erosion effect in the selected site utilizing correlation between the difference $\Delta EE$ and an absolute value of the erosion effect;

presence of defects or corrosion effect in the structure;

presence of residue effect in the structure.

\* \* \* \* \*